(12) United States Patent
Urness et al.

(10) Patent No.: US 9,033,879 B2
(45) Date of Patent: May 19, 2015

(54) PORTABLE IMAGING SYSTEM WITH REMOTE ACCESSIBILITY

(75) Inventors: Mark Steven Urness, Wauwatosa, WI (US); Brent Lavin, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/023,117

(22) Filed: Feb. 8, 2011

(65) Prior Publication Data

US 2012/0203104 A1  Aug. 9, 2012

(51) Int. Cl.
*A61B 8/00* (2006.01)
*A61B 8/08* (2006.01)

(52) U.S. Cl.
CPC .............. *A61B 8/4427* (2013.01); *A61B 8/4472* (2013.01); *A61B 8/465* (2013.01); *A61B 8/467* (2013.01); *A61B 8/483* (2013.01)

(58) Field of Classification Search
None
See application file for complete search history.

(56) References Cited

U.S. PATENT DOCUMENTS

| | | | | |
|---|---|---|---|---|
| 5,715,823 | A * | 2/1998 | Wood et al. | 600/437 |
| 5,976,088 | A * | 11/1999 | Urbano et al. | 600/443 |
| 6,353,445 | B1 * | 3/2002 | Babula et al. | 715/733 |
| 6,440,071 | B1 * | 8/2002 | Slayton et al. | 600/437 |
| 6,511,426 | B1 * | 1/2003 | Hossack et al. | 600/437 |
| 6,603,494 | B1 * | 8/2003 | Banks et al. | 715/807 |
| 6,633,833 | B2 * | 10/2003 | Sharma et al. | 702/188 |
| 6,687,736 | B1 | 2/2004 | Lee | |
| 6,733,449 | B1 * | 5/2004 | Krishnamurthy et al. | 600/437 |
| 7,246,264 | B2 * | 7/2007 | Grellmann et al. | 714/25 |
| 7,457,672 | B2 * | 11/2008 | Katsman et al. | 700/17 |
| 7,500,952 | B1 * | 3/2009 | Chiang et al. | 600/446 |
| 7,583,190 | B2 | 9/2009 | Reggiardo et al. | |
| 7,691,063 | B2 * | 4/2010 | Peteresen et al. | 600/447 |
| 7,787,678 | B2 * | 8/2010 | Unal et al. | 382/128 |
| 8,021,300 | B2 * | 9/2011 | Ma et al. | 600/437 |
| 8,155,406 | B2 * | 4/2012 | Mattiuzzi | 382/128 |
| 8,241,217 | B2 * | 8/2012 | Chiang et al. | 600/447 |
| 8,243,940 | B2 * | 8/2012 | Smith | 381/67 |
| 8,626,953 | B2 * | 1/2014 | Bucholz | 709/249 |
| 8,790,263 | B2 * | 7/2014 | Randall et al. | 600/455 |
| 8,849,679 | B2 * | 9/2014 | Wang et al. | 705/2 |
| 2003/0182458 | A1 | 9/2003 | Ali et al. | |
| 2006/0084872 | A1 * | 4/2006 | Ichikawa et al. | 600/437 |
| 2006/0288270 | A1 | 12/2006 | Gaurav et al. | |
| 2007/0004980 | A1 * | 1/2007 | Warner et al. | 600/411 |

(Continued)

FOREIGN PATENT DOCUMENTS

CN  1694408 A  11/2005
CN  101569539 A  11/2009

OTHER PUBLICATIONS

Butner et al, "A Real-time System for Tele-Surgery", IEEE 1063-6927/0, p. 236-243.*

(Continued)

*Primary Examiner* — Nicholas Evoy
(74) *Attorney, Agent, or Firm* — Dean Small; The Small Patent Law Group, LLC (57) ABSTRACT

A portable ultrasound imaging system is provided. The system includes a probe for acquiring ultrasound image data. A memory stores the acquired ultrasound image data. A processor generates an image based on the stored ultrasound image data. A presentation layer is provided for remotely accessing the generated image to display the generated image at a remote location.

19 Claims, 8 Drawing Sheets

(56) References Cited

U.S. PATENT DOCUMENTS

| | | | |
|---|---|---|---|
| 2007/0179811 A1* | 8/2007 | Reiner | 705/2 |
| 2007/0265531 A1* | 11/2007 | He et al. | 600/454 |
| 2007/0269017 A1* | 11/2007 | Umeki et al. | 378/165 |
| 2008/0060009 A1 | 3/2008 | Kelts | |
| 2008/0082966 A1* | 4/2008 | Dorn et al. | 717/120 |
| 2008/0146940 A1* | 6/2008 | Jenkins et al. | 600/463 |
| 2008/0146943 A1* | 6/2008 | Jenkins et al. | 600/466 |
| 2008/0175453 A1* | 7/2008 | Hao et al. | 382/128 |
| 2008/0228522 A1* | 9/2008 | Davis et al. | 705/2 |
| 2008/0269613 A1* | 10/2008 | Summers et al. | 600/459 |
| 2008/0300490 A1* | 12/2008 | Chiang et al. | 600/459 |
| 2009/0015665 A1* | 1/2009 | Willsie | 348/77 |
| 2009/0018441 A1* | 1/2009 | Willsie et al. | 600/437 |
| 2009/0048513 A1* | 2/2009 | Friedman et al. | 600/437 |
| 2009/0112091 A1* | 4/2009 | Chiang et al. | 600/447 |
| 2009/0204003 A1* | 8/2009 | Guracar | 600/458 |
| 2009/0259490 A1* | 10/2009 | Colang et al. | 705/3 |
| 2009/0264753 A1* | 10/2009 | von Schulthess et al. | 600/431 |
| 2009/0306505 A1* | 12/2009 | Yoshikawa et al. | 600/443 |
| 2009/0307328 A1* | 12/2009 | Nuttall et al. | 709/212 |
| 2009/0312638 A1* | 12/2009 | Bartlett | 600/443 |
| 2010/0016716 A1* | 1/2010 | Hyun | 600/437 |
| 2010/0022882 A1* | 1/2010 | Duckworth et al. | 600/447 |
| 2010/0036676 A1* | 2/2010 | Safdi et al. | 705/2 |
| 2010/0049046 A1* | 2/2010 | Peiffer et al. | 600/443 |
| 2010/0088346 A1 | 4/2010 | Urness et al. | |
| 2010/0138523 A1 | 6/2010 | Urness et al. | |
| 2010/0228130 A1* | 9/2010 | Chiang et al. | 600/447 |
| 2010/0280375 A1* | 11/2010 | Zhang et al. | 600/443 |
| 2011/0125022 A1* | 5/2011 | Lazebnik | 600/444 |
| 2012/0053597 A1* | 3/2012 | Anvari et al. | 606/130 |
| 2012/0053962 A1* | 3/2012 | Routh et al. | 705/2 |
| 2012/0071710 A1* | 3/2012 | Gazdzinski | 600/101 |
| 2012/0157846 A1* | 6/2012 | Li et al. | 600/443 |
| 2012/0179035 A1* | 7/2012 | Boudier | 600/439 |
| 2013/0083981 A1* | 4/2013 | White et al. | 382/128 |
| 2014/0039277 A1* | 2/2014 | Abraham | 600/301 |

OTHER PUBLICATIONS

Pyke et al, "A Tele-ultrasound System for Real-time Medical Imaging in Resource-limited Settings", Proceedings of the 29th Annual International, Conference of the IEEE EMBS, Cité Internationale, Lyon, France, Aug. 23-26, 2007.*

Suenaga et al, "A Tele-Instruction System for Ultrasound Probe Operation Based on Shared AR Technology", 2001 Proceedings of the 23rd Annual EMBS International Conference, Oct. 25-28, Istanbul, Turkey.*

Cabral Jr., Ultrasound telemedicine system supporting compression of pre-scan-converted data, In Medical Imaging 2000: Image Display and Visualization, Seong K. Mun, 350 Editor, Proceedings of SPIE vol. 3976 (2000).*

Popov et al., The Feasibility of Real-Time Transmission of Sonographic Images from a Remote Location over Low-Bandwidth Internet Links: A Pilot Study, AJR 2007; 188:W219-W222 (Mar. 2007).*

Solano et al., Asynchronous Telemedicine with Ultrasound: Improving Maternal Health in Developing Countries, 2009 IEEE International Ultrasonics Symposium Proceedings.*

Sublett et al., Design and Implementation of a Digital Teleultrasound System for Real-Time Remote Diagnosis, Eighth IEEE Symposium on Computer-Bused Medical Systems (1995).*

Unofficial translation of CN Search Report from corresponding CN Patent Application No. 2012100346477 dated Sep. 16, 2014.

* cited by examiner

PORTABLE IMAGING SYSTEM WITH REMOTE ACCESSIBILITY

BACKGROUND OF THE INVENTION

The subject matter described herein relates generally to imaging systems, and more particularly, to portable imaging systems.

Ultrasound imaging systems are used in different applications to image different regions or areas (e.g. different organs) of patients or other objects. For example, an ultrasound imaging system may be utilized to generate an image of organs, vasculature, heart, or other portions of the body. Ultrasound imaging systems are generally located at a medical facility, for example, a hospital or imaging center. However, not all people have access to a medical facility. In particular, individuals at nursing homes, under home care, or in rural areas may not be capable of attending a medical facility for ultrasound imaging.

Portable ultrasound imaging systems may be utilized to acquire images of a patient at locations remote from a medical facility. For example, the portable ultrasound imaging system acquires imaging data at the remote location that then may be provided to the medical facility. Thereafter, the imaging data is used to generate an image at the medical facility. However, known portable ultrasound imaging systems generally provide one way communication with the medical facility. In particular, the imaging data is only capable of being extracted from the portable ultrasound imaging system and sent to the medical facility. Extracting the imaging data is commonly performed by downloading the imaging data onto a data disc or other media that is mailed to the medical facility. The data disc includes confidential patient information that may be protected under HIPPA regulations. However, such discs are typically unprotected and may create privacy issues if the disc is lost, stolen, or not properly destroyed after use.

SUMMARY OF THE INVENTION

In one embodiment, a portable ultrasound imaging system is provided. The system includes a probe for acquiring ultrasound image data. A memory stores the acquired ultrasound image data. A processor generates an image based on the stored ultrasound image data. A presentation layer is provided for remotely accessing the generated image to display the generated image at a remote location.

In another embodiment, a method for displaying an image from a portable ultrasound imaging system is provided. The method includes acquiring ultrasound image data with a portable ultrasound imaging system. The acquired ultrasound image data is stored in a memory within the portable ultrasound imaging system. An image is generated based on the stored ultrasound image data. The generated image is remotely accessed to display the generated image at a remote location.

In another embodiment, an imaging system is provided. The system includes an imaging device having a scanning device for acquiring imaging data. A memory stores the acquired image data. A processor generates an image based on the stored image data. A presentation layer displays the generated image. A display is located at a remote location from the imaging device. The display remotely accesses the presentation layer to display the generated image at the remote location.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. One or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

At least one technical effect of the various embodiments is providing remote access to image data stored on a portable ultrasound imaging system. The portable ultrasound imaging system can be used at locations remote from a medical facility. For example, the portable ultrasound imaging system may be used at a nursing home, in a rural area, or the like. Image data is acquired with the portable ultrasound imaging system at the remote location. The image data is stored within a memory provided in the portable ultrasound imaging system. A presentation layer provided within the portable ultrasound imaging system displays an image associated with the image data that has been processed and generated. The presentation layer is remotely accessible through a network or web-based browser. At the medical facility, images associated with the image data may be viewed and manipulated, however the image data itself is not transferred to the medical facility. Rather, the image data remains securely protected within the memory of the ultrasound imaging system.

Although the various embodiments are described with respect to an ultrasound imaging system, the various embodiments may be utilized with any suitable imaging system, for example, X-ray, computed tomography, single photon emission computed tomography, magnetic resonance imaging, or the like.

Figure 1:
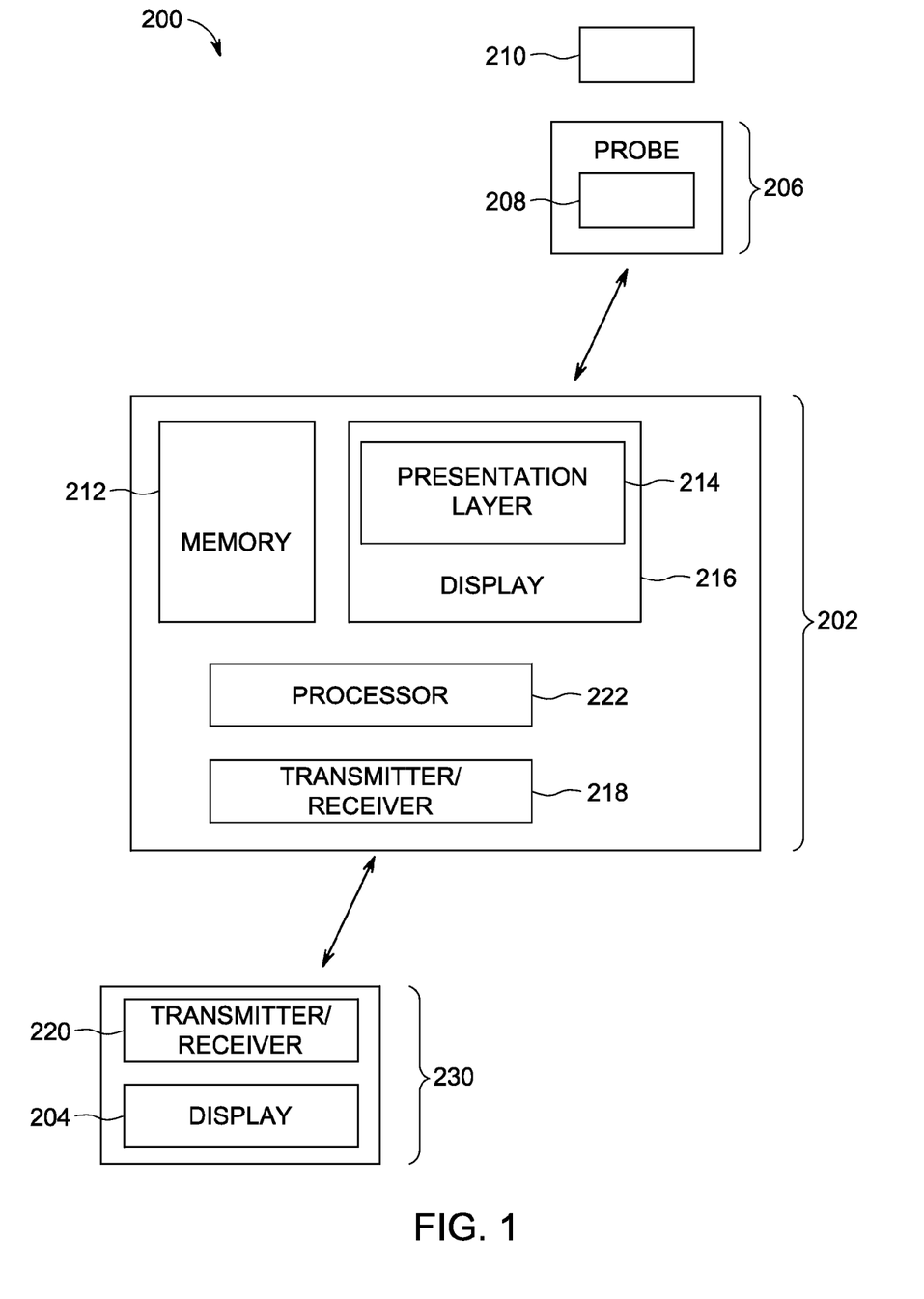
FIG. 1 is a schematic block diagram of an imaging system formed in accordance with an embodiment.

FIG. 1 is a schematic view of an imaging system 200 including an ultrasound imaging system 202 and a workstation 230. The ultrasound imaging system 202 may be a portable ultrasound imaging system, such as the systems 600, 650, and 700 shown in FIGS. 6, 7, and 8 respectively. The ultrasound imaging system 202 may be transportable to a remote location, such as a nursing home, rural area, or the like. Thus, the ultrasound imaging system 202 is located remotely from the workstation 230. For example, the workstation 230 may be positioned at a location, such as a hospital, imaging center, or other medical facility. The workstation 230 may be a computer, tablet-type device, or the like. The workstation 230 may be any type of computer or end user device. The workstation 230 includes a display 204. The workstation 230 communicates with the ultrasound imaging system 202 to display an image based on image data acquired by the ultrasound imaging system 202 on the display 204. The workstation 230 also includes any suitable components image viewing, manipulation, etc.

A probe 206 is in communication with the ultrasound imaging system 202. The probe 206 may be mechanically coupled to the ultrasound imaging system 202. Alternatively, the probe 206 may wirelessly communicate with the imaging system 202. The probe 206 includes transducer elements 208 that emit ultrasound pulses to an object 210 to be scanned, for example an organ of a patient. The ultrasound pulses may be back-scattered from structures within the object 210, such as blood cells or muscular tissue, to produce echoes that return to the transducer elements 208. The transducer elements 208 generate ultrasound image data based on the received echoes. The probe 206 transmits the ultrasound image data to the ultrasound imaging system 202.

The ultrasound imaging system 202 includes a memory 212 that stores the ultrasound image data. The memory 212 may be a database, random access memory, or the like. In one embodiment, the memory 212 is a secure encrypted memory that requires a password or other credentials to access the image data stored therein. The memory 212 may have multiple levels of security. For example, a surgeon or doctor may have access to all of the data stored in the memory 212, whereas, a technician may have limited access to the data stored in the memory 212. In one embodiment, a patient may have access to the ultrasound image data related to the patient, but is restricted from all other data.

A processor 222 accesses the ultrasound image data from the memory 212. The processor 222 may be a logic based device, such as one or more computer processors or microprocessors. The processor 222 generates an image based on the ultrasound image data. The image is displayed on a presentation layer 214, which may be, for example, a graphical user interface (GUI) or other displayed user interface, such as a virtual desktop. The presentation layer 214 may be a software based display that is accessible from multiple locations. The presentation layer 214 displays the image on a display 216 provided within the ultrasound imaging system 202. Alternatively, the presentation layer 214 may be accessible through a web-based browser, local area network, or the like. In such an embodiment, the presentation layer 214 may be accessible remotely as a virtual desktop that displays the presentation layer 214 in the same manner as the presentation layer 214 is displayed on the display 216.

The ultrasound imaging system 202 also includes a transmitter/receiver 218 that communicates with a transmitter/receiver 220 of the workstation 230. The ultrasound imaging system 202 and the workstation 230 communicate through the transmitter/receivers 218 and 220, respectively. The ultrasound imaging system 202 and the workstation 230 may communicate over a local area network. For example, the ultrasound imaging system 202 and the workstation 230 may be positioned in separate remote locations of a medical facility and communicate over a network provided at the facility. In an exemplary embodiment, the ultrasound imaging system 202 and the workstation 230 communicate over an internet connection, such as through a web-based browser.

An operator may remotely access imaging data stored on the ultrasound imaging system 202 from the workstation 230. For example, the operator may log onto a virtual desktop or the like provided on the display 204 of the workstation 230. The virtual desktop remotely links to the presentation layer 214 of the ultrasound imaging system 202 to access the memory 212 of the ultrasound imaging system 202. The memory 212 may be secured and encrypted to limit access to the image data stored therein. The operator may input a password to gain access to at least some of the image data.

Once access to the memory 212 is obtained, the operator may select image data to view. It should be noted that the image data is not transferred to the workstation 230. Rather, the image data is processed by the processor 222 to generate an image on the presentation layer 214. For example, the processor 222 may generate a DICOM image on the presentation layer 214. The ultrasound imaging system 202 transmits the presentation layer 214 to the display 204 of the workstation 230 so that the presentation layer 214 is viewable on the display 204.

In one embodiment, the workstation 230 may be used to manipulate the image on the presentation layer 214. The workstation 230 may be used to change an appearance of the image, such as rotate the image, enlarge the image, adjust the contrast of the image, or the like. Moreover, an image report may be input at the workstation 230. For example, an operator may input notes, analysis, and/or comments related to the image. In one embodiment, the operator may input landmarks or other notations on the image. The image report is then saved to the memory 212 of the ultrasound imaging system 202.

Accordingly, the operator can access images remotely and provide analysis of the images without transferring the image data from the ultrasound imaging system 202. The image data remains stored only on the ultrasound imaging system 202 so that the data remains restricted only to individuals with proper certification.

In one embodiment, the ultrasound imaging system 202 is capable of simultaneous scanning and image data acquisition. The ultrasound imaging system 202 may be utilized to acquire a first set of imaging data, while a second set of imaging data is accessed to display on the display 204 of the workstation 230 an image based on the second set of imaging data.

Figure 2:
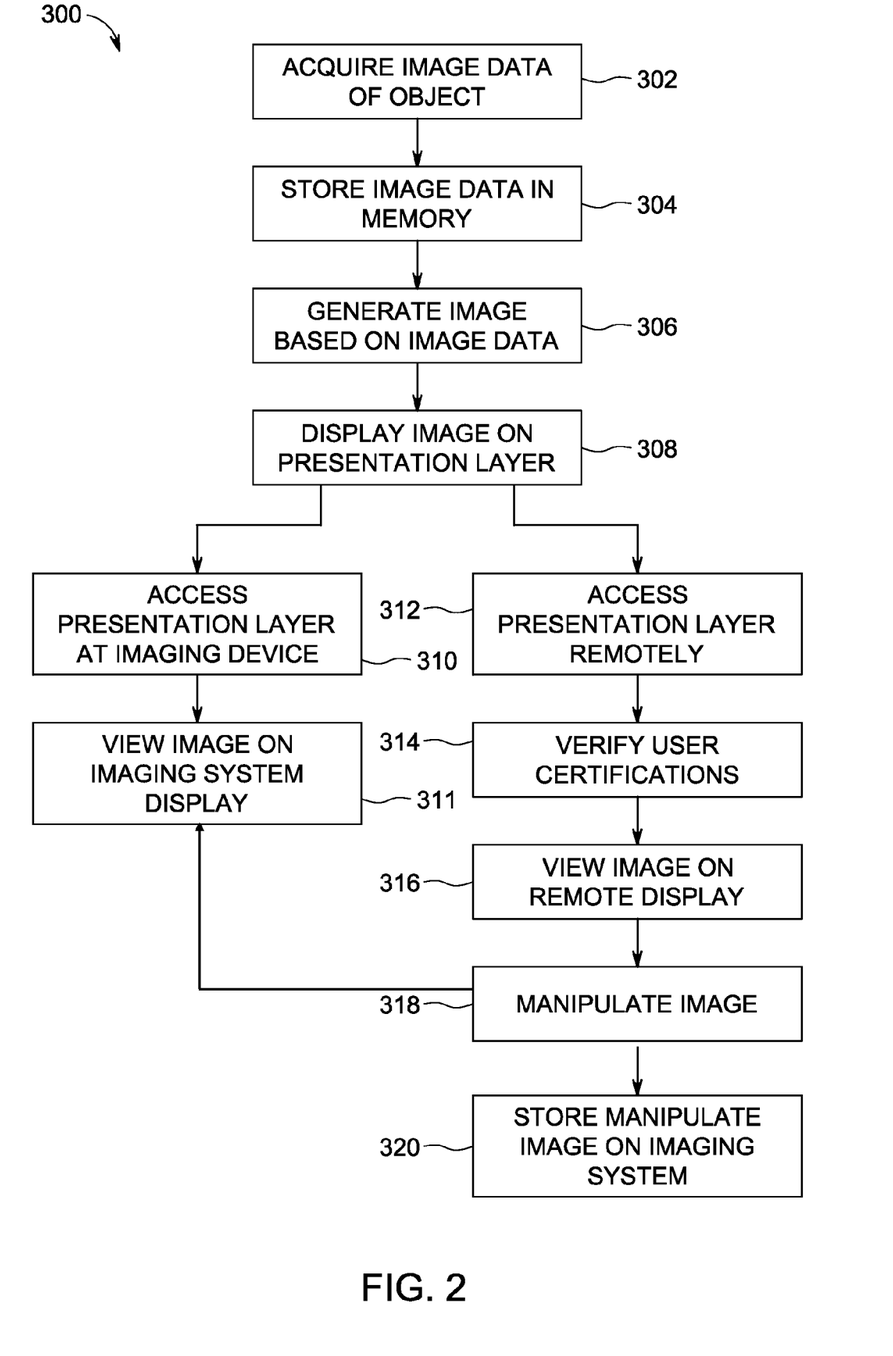
FIG. 2 is a flowchart of a method for operating the imaging system shown in FIG. 1 in accordance with an embodiment.

FIG. 2 illustrates a method 300 for operating the imaging system 200. At 302, image data of the object 210 is acquired using the ultrasound imaging system 202. The image data acquired may be two-dimensional or three-dimensional image data. In one embodiment, the ultrasound imaging system 202 may acquire four-dimensional image data. In an exemplary embodiment, the image data is acquired with the probe 206 and transmitted to the ultrasound imaging system 202. At 304, the image data is stored in the memory 212. The memory 212 may store the image data in files. For example, a file may be created in the memory 212 for all image data related to a particular patient. In another embodiment, a file may be created in the memory 212 for all image data that is to be viewed at a particular medical facility. Accordingly, access to the image data may be limited to particular files.

At 306, the processor 222 generates an image based on the image data stored in the memory 212, which may be generated, for example, when requested by a user/operator. The image is displayed in the presentation layer 214, at 308. At 310, an operator may access the image at the ultrasound imaging system 202. The image is then displayed on the display 216 at 311.

Alternatively, at 312, the presentation layer 214 may be remotely accessed at the workstation 230. The presentation layer 214 may be accessed through a network, web-based browser, or the like. The presentation layer 214 may be displayed on the display 204 as a virtual desktop. In an exemplary embodiment, the presentation layer 214 displays a first image that may be remotely accessed at the workstation 230, while an operator simultaneously views a second image on a second presentation layer 214 displayed at the display 216 of the ultrasound imaging system 202. It should be noted that multiple workstations 230 may concurrently access image data stored in the memory 212. Additionally, multiple windows or display regions may be provided at the workstation 230.

To access the image data through the presentation layer 214, user credentials must first be verified at 314. The user credentials may be verified by entering a password. Individuals accessing the image data may have varying credentials. For example, a surgeon, doctor, or the like may have access to any of the image data stored in the memory. The access of technicians and staff may be limited to the image data related to a particular patient and/or image data stored in a particular file. In one embodiment, patients may be able to access their own image data. After the user credentials are verified, at 314, an image based on the image data and generated to the ultrasound system 202 is displayed on the display 204 of the workstation 230 at 316. However, the image data itself is not transferred to the workstation. The image data remains confidentially and securely stored in the memory 212 of the ultrasound imaging system 202.

At 318, the image on the display 204 may optionally be manipulated. The image may be manipulated to alter an appearance of the image. In one embodiment, landmarks or other indicators may be placed on the image. An image report may also be entered at the workstation 230. The image report may include a doctor or technician's analysis of the image. At 320, the altered image and/or the image report may be saved to the memory 212. The altered image and/or image report may then be remotely accessed at 312 via the presentation layer 214 at a later time and/or from another location. The steps 312-320 may be performed to view and alter a first image based on first image data, while the step 302 is concurrently performed to acquire second image data.

Figure 3:
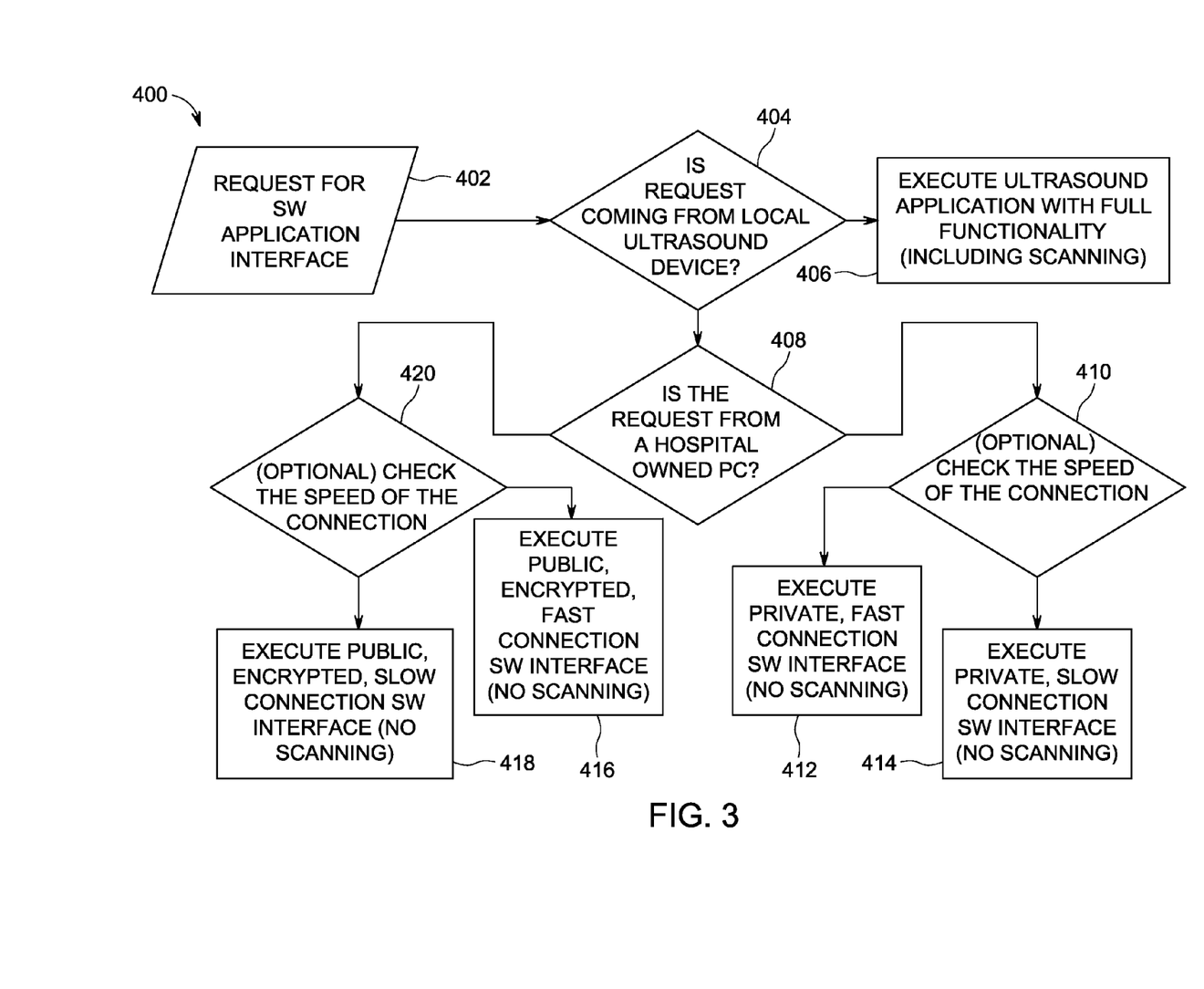
FIG. 3 is a flowchart of a method for accessing the ultrasound imaging system shown in FIG. 1 in accordance with an embodiment.

FIG. 3 illustrates a method 400 for accessing the ultrasound imaging system 202 and verifying credentials. At 402, a request is made to access the presentation layer 214 of the ultrasound imaging system 202. The ultrasound imaging system 202 determines at 404 if the request is being made from the display 216 of the ultrasound imaging system 202. If the request is being made from the display 216 of the ultrasound imaging system 202 the operator is granted access at 406 to the full functionality of the ultrasound imaging system 202. Access to the full functionality of the ultrasound imaging system enables the operator to both perform scans with the ultrasound imaging system 202 and to view images on the presentation layer 214.

If the request is not being made from the display 216 of the ultrasound imaging system 202, the system 202 determines at 408 whether the request is being made from a medical facility. If the request is being made from a medical facility, the ultrasound imaging system 202 may optionally determine a speed of the connection to the ultrasound imaging system at 410. At 412 and 414, private access to the memory 212 of the ultrasound imaging system 202 is granted, for example, using a virtual private network (VPN). At 412, fast access is granted based on a determined high-speed connection to the ultrasound imaging system 202. At 414, slow access is granted based on a determined slow-speed connection to the ultrasound imaging system 202. The private access granted at 412 and 414 may include access to all of the image data stored in the memory 212. Alternatively, the private access may include all of the image data stored for the particular medical facility. The private access granted at 412 and 414 may be limited to viewing images on the presentation layer 214.

If the request is not being made from a medical facility, the ultrasound imaging system 202 may grant public access to the image data, at 416 and 418. First at 420 the ultrasound imaging system 202 may determine a connection speed to the ultrasound imaging system 202. At 416, fast access is granted based on a determined high-speed connection to the ultrasound imaging system 202. At 418, slow access is granted based on a determined slow-speed connection to the ultrasound imaging system 202. The public access granted at 416 and 418 may limit the image data that is accessible from the ultrasound imaging system 202. For example, a patient may obtain public access from home to view the patient's image data. Alternatively, a doctor's office may receive limited access to the image data of a particular patient.

In the various embodiments, all of the image data may be encrypted and password protected. The ultrasound imaging system 202 may be configured to grant various layers of access to the image data. Access to the image data is controlled at the ultrasound imaging system 202 based on an operator's credentials. For example, a doctor requesting a scan of a patient may be provided with an access code prior to the exam. After the scan is completed, the doctor may access the image data using the access code. In another embodiment, the ultrasound imaging system 202 may be the property of a hospital or other medical facility. The hospital may configure the ultrasound imaging system 202 with a plurality of access codes that are selectively provided to employees of the hospital. The image data is stored solely in the memory 212 of the ultrasound imaging system 202. Accordingly, the image data is viewable at remote locations, but remains protected from public disclosure, copying, destruction, or the like.

Figure 4:
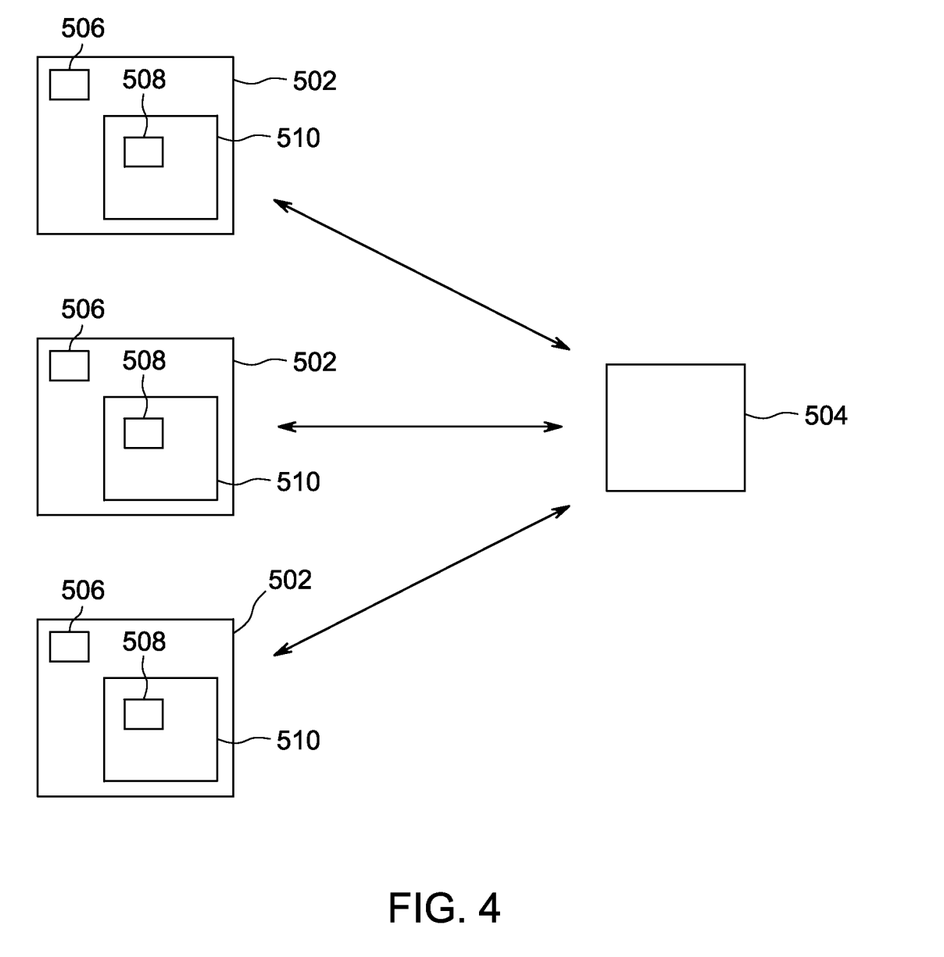
FIG. 4 is a schematic block diagram of an imaging network formed in accordance with an embodiment.

FIG. 4 is a schematic view of an imaging network 500 formed in accordance with an embodiment. The imaging network 500 includes a plurality of imaging devices 502 and a single workstation 504. At least some of the imaging devices 502 may be portable imaging devices. The imaging devices 502, which may be portable devices, may be used at a remote location to scan patients that are unable to have imaging performed at a medical facility. Alternatively, at least some of the imaging devices 502 may be fixed devices at a remote location. For example, the imaging devices 502 may be console-type ultrasound systems located in a remote area that has limited access to doctors. The imaging devices 502 may be used to scan patients at the remote area so that a doctor at a medical facility can read an image based on the acquired image data. In an alternative embodiment, at least some of the imaging devices 502 may be imaging devices positioned in a remote location of a medical facility.

In one embodiment, the imaging devices 502 may be portable ultrasound imaging systems, such as the ultrasound imaging system 200 (shown in FIG. 1). In one embodiment, the imaging devices 502 may include any known imaging device, for example, X-ray, computed tomography, single photon emission computed tomography, magnetic resonance imaging, or the like.

Each of the imaging devices 502 includes a memory 506 to store image data acquired by the imaging device 502. The memory 506 may be a secure encrypted memory that limits access to the image data. A presentation layer 508 is provided within each imaging device 502 to display images based on the image data stored in the memory 506. The presentation layer 508 may be displayed on a user interface 510 provided at the imaging device 502. In one embodiment, the presentation layer 508 of each imaging device 502 is remotely accessible through a network, the internet, or the like.

The workstation 504 is located remotely from the imaging devices 502. The workstation 504 may be located at a medical facility, such as a doctor's office, hospital, or the like, or may be located at an individual's home or office. Although, the illustrated embodiment includes only one workstation 504, multiple workstations 504 may be provided in the network 500. The workstation 504 (e.g. a computer, tablet-type device, or the like) may be used to remotely access the image data stored on any of the imaging devices 502. The workstation 504 is used to access the presentation layer 508 of any of the imaging devices 502. The presentation layers 508 are accessed through a network, the internet, or the like. In one embodiment, the presentation layers 508 are accessed through a web-based browser. The presentation layers 508 may be displayed at the workstation 504 as a virtual desktop.

An operator at the workstation 504 may access the image data stored on any of the imaging devices 502 based on the operator's credentials. Some operators may have access to any image data, while other operators may have limited access to the image data. By having access to the image data stored on any of the imaging devices 502, multiple imaging procedures may be performed at various locations and all of the images may be accessible from a single workstation 504. For example, a doctor may order both ultrasound and X-ray scans of a patient on separate imaging devices 502. The ultrasound and the X-ray image data may be acquired at different locations. However, the doctor can have access to both the X-ray image data and the ultrasound image data at a single workstation 504.

Figure 5:
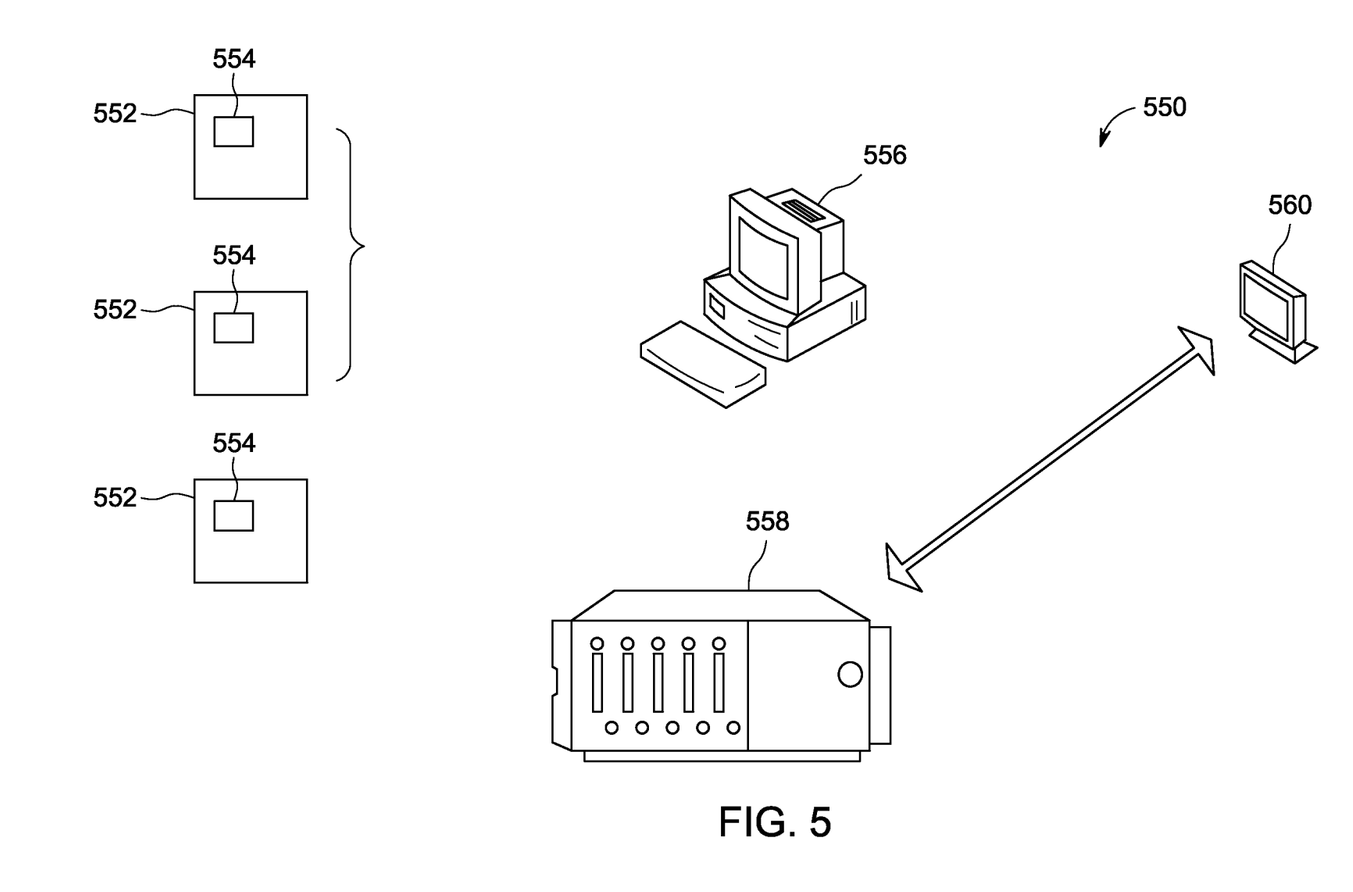
FIG. 5 is a schematic block diagram of an imaging network formed in accordance with another embodiment.

FIG. 5 is a schematic view of an imaging network 550 formed in accordance with another embodiment. The imaging network 550 includes a plurality of imaging devices 552. Each of the imaging devices 552 includes a memory 554 to store image data acquired with the imaging device 552. The imaging devices 552 generate images based on the acquired image data. The images from each imaging device 552 are transmitted to a central hub 556. The central hub 556 stores each image in a memory 558. The memory 558 may be a database, an archive, or the like. The memory 558 may be a secured and encrypted memory.

A workstation 560 is located remotely from the imaging devices 552 and the memory 558. The workstation 560 may be used to access the images in the memory 558. The workstation 560 accesses the images in the memory in the same manner as described with respect to accessing an imaging system as described in FIGS. 1-4. The image data remains stored in the imaging devices 552 and is not transmitted to the workstation 560.

Figure 6:
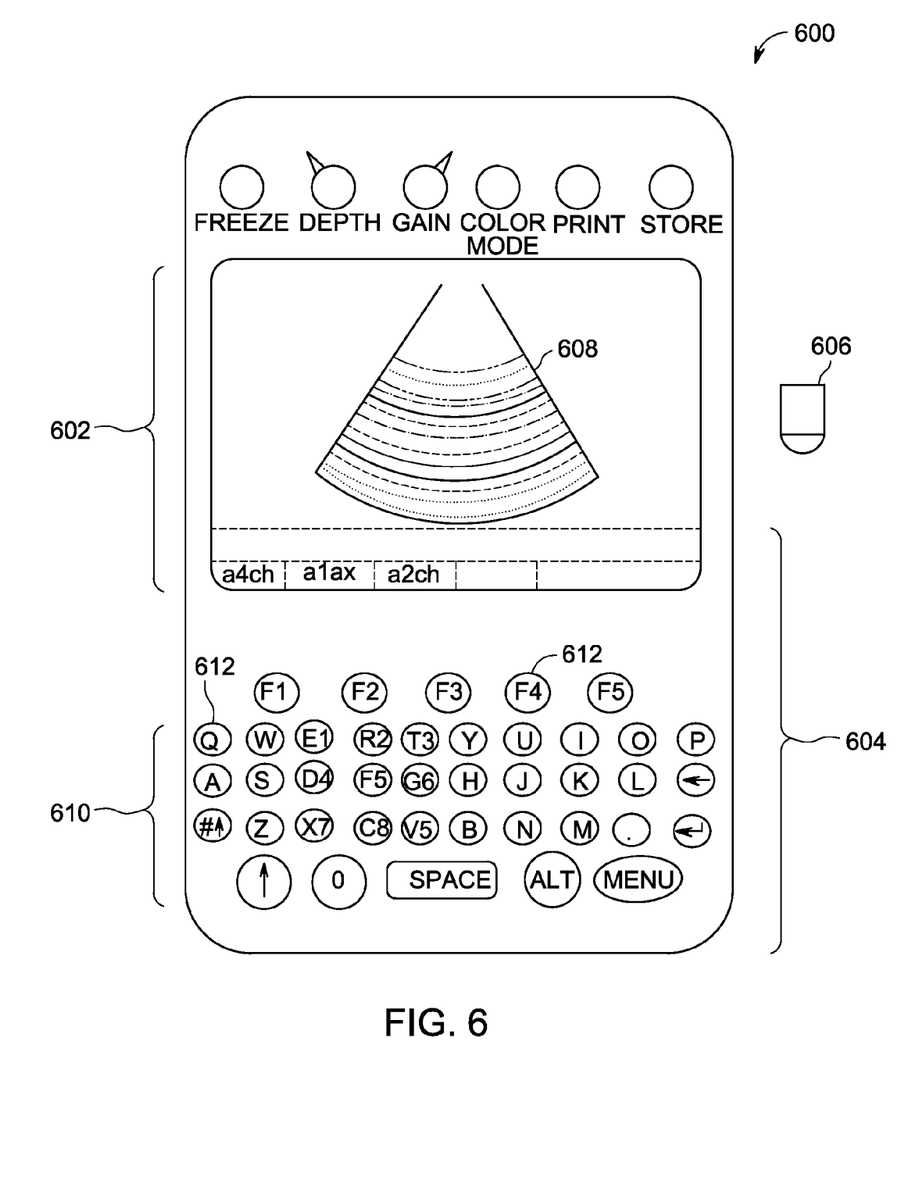
FIG. 6 is a perspective view of a hand carried or pocket-sized ultrasound imaging system formed in which various embodiments may be implemented.

FIG. 6 illustrates a hand carried or pocket-sized ultrasound imaging system 600 having a display 602 (which may be embodied as the display 216) and a user interface 604 formed in a single unit. The imaging system 600 may be used to acquire ultrasound image data at a location that is remote from a medical facility. The ultrasound imaging system 600 may be configured to operate as described in FIGS. 1-3. By way of example, the ultrasound imaging system 600 may be approximately two inches wide, approximately four inches in length, and approximately half an inch in depth. The ultrasound imaging system may weigh approximately three ounces. The ultrasound imaging system 600 generally includes the display 602 and the user interface 604, which may or may not include a keyboard-type interface and an input/output (I/O) port for connection to a scanning device, for example, an ultrasound probe 606. The display 602 may be, for example, a 320×320 pixel color LCD display on which a medical image 608 may be displayed. A typewriter-like keyboard 610 of buttons 612 may optionally be included in the user interface 604.

The probe 606 may be coupled to the system 600 with wires, cable, or the like. Alternatively, the probe 606 may be physically or mechanically disconnected from the system 600. The probe 606 may wirelessly transmit acquired ultrasound data to the system 600 through an access point device (not shown), such as an antenna disposed within the system 600.

Figure 7:
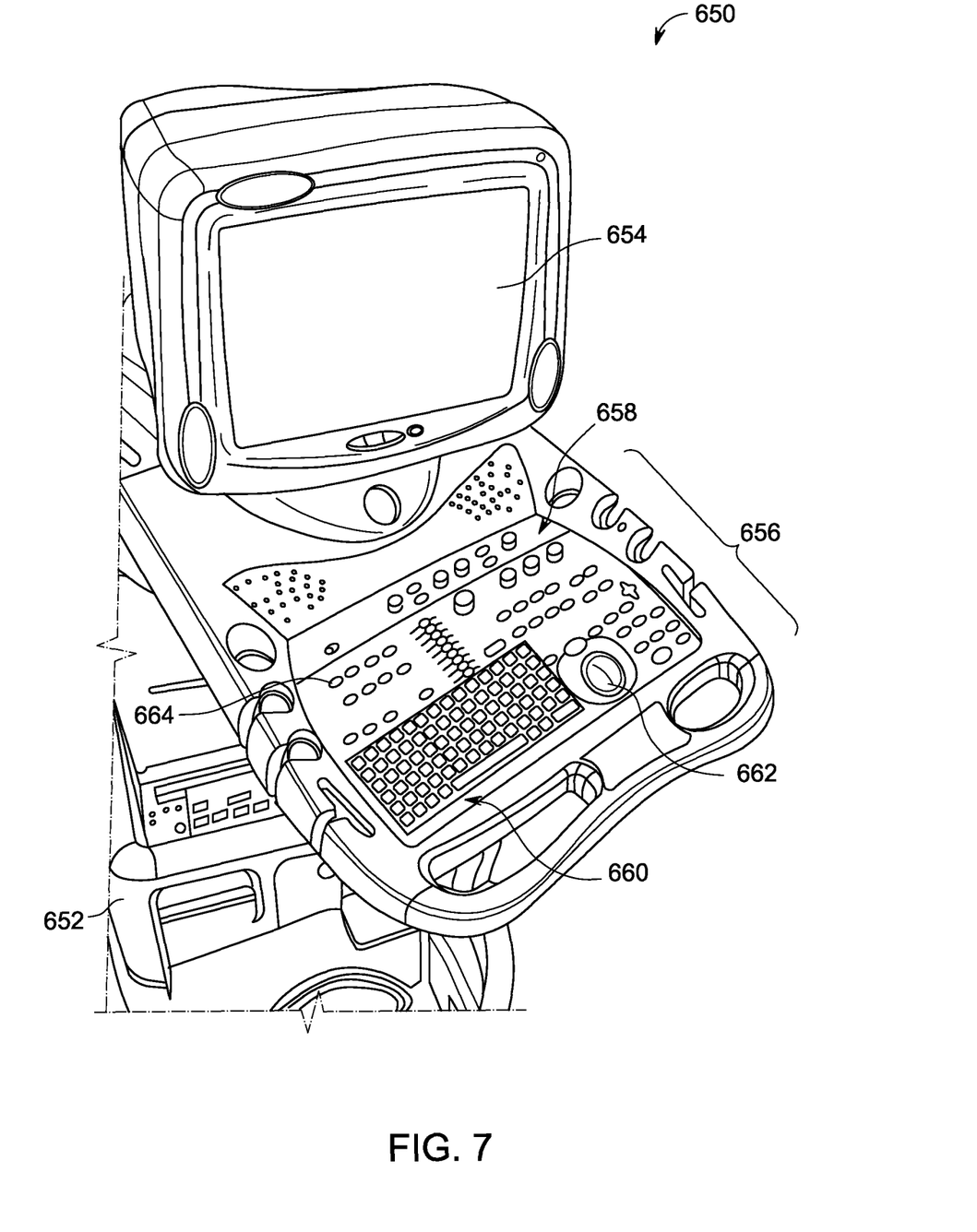
FIG. 7 is a perspective view an ultrasound imaging system in which various embodiments may be implemented.

FIG. 7 illustrates an ultrasound imaging system 650 provided on a moveable base 652. The ultrasound imaging system 650 may be configured to operate as describe in FIGS. 1-3. The system 650 may be used to acquire ultrasound image data at a location that is remote from a medical facility. A display 654 (which may be embodied as the display 216) and a user interface 656 are provided and it should be understood that the display 654 may be separate or separable from the user interface 656. The user interface 656 may optionally be a touchscreen, allowing an operator to select options by touching displayed graphics, icons, and the like.

The user interface 656 also includes control buttons 658 that may be used to control the system 650 as desired or needed, and/or as typically provided. The user interface 656 provides multiple interface options that the user may physically manipulate to interact with ultrasound data and other data that may be displayed, as well as to input information and set and change scanning parameters and viewing angles, etc. For example, a keyboard 660, trackball 662, and/or other multi-function controls 664 may be provided. One or more probes (such as the probe 606 shown in FIG. 1) may be communicatively coupled with the system 650 to transmit acquired ultrasound data to the system 650.

Figure 8:
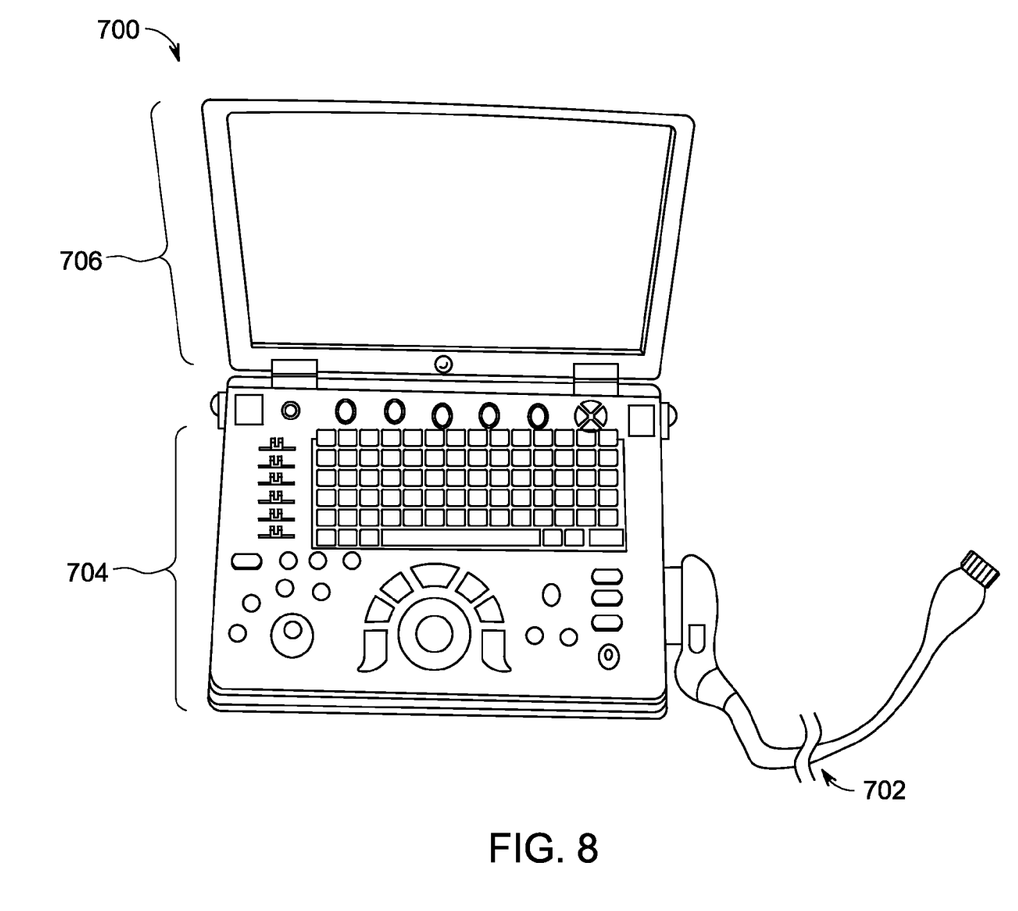
FIG. 8 is a perspective view of a three-dimensional (3D) capable miniaturized ultrasound system in which various embodiments may be implemented.

FIG. 8 illustrates a 3D-capable miniaturized ultrasound system 700 having a probe 702 that may be configured to acquire 3D ultrasonic data or multi-plane ultrasonic data. A user interface 704 including an integrated display 706 (which may be embodied as the display 216) is provided to receive commands from an operator. As used herein, "miniaturized" means that the ultrasound system 700 is a handheld or hand-carried device or is configured to be carried in a person's hand, pocket, briefcase-sized case, or backpack. For example, the ultrasound system 700 may be a hand-carried device having a size of a typical laptop computer. The ultrasound system 700 is easily portable by the operator. The integrated display 706 (e.g., an internal display) is configured to display, for example, one or more medical images.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the described subject matter without departing from their scope. While the dimensions and types of materials described herein are intended to define the parameters of the various embodiments of the invention, the embodiments are by no means limiting and are exemplary embodiments. Many other embodiments will be apparent to one of ordinary skill in the art upon reviewing the above description. The scope of the various embodiments of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable one of ordinary skill in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A portable ultrasound imaging device comprising:
   a housing;
   a display electrically connected to the housing;
   a probe communicatively coupled to the housing via at least one of a mechanical connection or a wireless connection, the probe configured to acquire ultrasound image data from an object during an ultrasound imaging scan;
   a memory within the housing, the memory configured to store the ultrasound image data acquired during the scan;
   one or more processors within the housing the one or more processors configured to access at least a subset of the ultrasound image data stored in the memory in response to a request received from a remote workstation that is remotely located relative to the ultrasound imaging device, the one or more processors further configured to generate at least one ultrasound image on a presentation layer, the at least one ultrasound image generated based on the subset of the ultrasound image date; and
   a transmitter and receiver electrically connected to the housing, the receiver configured to receive the request from the remote workstation, the transmitter further configured to transmit the presentation layer to the remote workstation such that the at least one ultrasound image is viewable at the remote workstation without transmitting the subset of the ultrasound image data used to generate the at least one ultrasound image, the subset of ultrasound image data remaining stored in the memory.

2. The device of claim 1, wherein the memory is a secure encrypted memory.

3. The device of claim 1, wherein the presentation layer comprises a software based display including a user interface forming a virtual desktop on a display at the remote workstation.

4. The device of claim 1, wherein a first ultrasound image generated by the one or more processors using a first subset of the ultrasound image data stored in the memory is transmitted to the remote workstation by the transmitter, while a second subset of the ultrasound image data is concurrently acquired with the probe and communicated to the memory during the ultrasound imaging scan.

5. The device of claim 1, wherein the presentation layer is transmitted to the remote workstation by the transmitter through at least one of a web-based browser or a local area network.

6. The device of claim 1, wherein the presentation layer is a first presentation layer that is viewable at the remote workstation as a virtual desktop, the display being configured to display a second presentation layer such that at least one ultrasound image is viewable at the portable ultrasound imaging device, the virtual desktop displaying the first presentation layer in the same manner as the second presentation layer is displayed on the display of the portable ultrasound imaging device.

7. The device of claim 1, wherein the presentation layer is transmitted by the transmitter to a central hub that is remotely interfaced with a plurality of imaging devices.

8. The device of claim 1, wherein the receiver is configured to receive an image report generated at the remote workstation, the image report being stored in the memory within the housing.

9. The device of claim 1, wherein the receiver is configured to receive an edited ultrasound image, the edited ultrasound image formed by manipulating, at the remote workstation, the at least one ultrasound image viewable at the remote workstation, the edited ultrasound image being stored in the memory.

10. A method for displaying an image from a portable ultrasound imaging device, the method comprising:
acquiring ultrasound image data from an object during an ultrasound imaging scan using a probe that is communicatively coupled to a housing of a portable ultrasound imaging device;
storing the ultrasound image data acquired during the scan in a memory within the housing of the ultrasound imaging device;
accessing at least a subset of the ultrasound image data stored in the memory in response to a request received from a remote workstation, the remote workstation being remotely located relative to the ultrasound imaging device;
generating at least one ultrasound image on a presentation layer, the at least one ultrasound image being generated based on the subset of the ultrasound image data; and
remotely accessing the generated image to display the generated image at a remote locationtransmitting the presentation layer to the remote workstation such that the at least one ultrasound image is viewable at the remote workstation without transmitting the subset of the ultrasound image data used to generate the at least one ultrasound image, the subset of ultrasound image data remaining stored in the memory.

11. The method of claim 10, wherein the memory in which the ultrasound image data is stored is a secure encrypted memory.

12. The method of claim 10, further comprising displaying the presentation layer on a display of the ultrasound imaging device, the display being electrically connected to the housing.

13. The method of claim 10, wherein the subset of the ultrasound image data used to generate the at least one ultrasound image on the presentation layer is a first subset of ultrasound image data, the method further comprising acquiring and storing a second subset of ultrasound image data during the ultrasound imaging scan, the second subset being acquired and stored concurrently to the presentation layer being transmitted to the remote workstation.

14. The method of claim 10, wherein the presentation layer is transmitted to the remote workstation through a web-based browser.

15. The method of claim 10, further comprising receiving an image report at the ultrasound imaging device from the remote workstation and storing the image report in the memory within the housing.

16. The method of claim 10, further comprising receiving an edited ultrasound image at the ultrasound imaging device from the remote workstation and storing the edited ultrasound image in the memory within the housing, the edited ultrasound image being formed by manipulating an appearance of the at least one ultrasound image viewable at the remote workstation on the presentation layer.

17. The device of claim 1, wherein the one or more processors are configured to verify user credentials before accessing the at least subset of the ultrasound image data stored in the memory, the one or more processor verifying the user credentials by at least one of a password received at the remote workstation or a source location of the request.

18. The device of claim 17, wherein the one or more processors are configured to access different subsets of the ultrasound image data stored in the memory based on the user credentials.

19. The device of claim 1, wherein the presentation layer transmitted by the transmitter to the remote workstation is a first presentation layer that includes a first ultrasound image, the display being configured to display a second presentation layer that includes a second ultrasound image, the second ultrasound image being viewable at the portable ultrasound imaging device.

* * * * *